(12) United States Patent  (10) Patent No.: US 8,225,015 B2
Gao-Saari et al.  (45) Date of Patent: Jul. 17, 2012

(54) SYSTEMS, METHODS, AND APPARATUS FOR MEDICAL DEVICE INTERFACE CONNECTIVITY

(75) Inventors: Lan Gao-Saari, Espoo (FI); Marko Raatikainen, Espoo (FI); Ilkka Vanhanen, Helsinki (FI); Jyrki Lindroos, Vantaa (FI); Juha Pärnänen, Helsinki (FI)

(73) Assignee: General Electric Company, Schenectady, NY (US)

( * ) Notice: Subject to any disclaimer, the term of this patent is extended or adjusted under 35 U.S.C. 154(b) by 94 days.

(21) Appl. No.: 12/484,868

(22) Filed: Jun. 15, 2009

(65) Prior Publication Data

US 2010/0318699 A1 Dec. 16, 2010

(51) Int. Cl.
*G06F 13/12* (2006.01)
(52) U.S. Cl. .......................................... 710/64; 710/8
(58) Field of Classification Search .................. None
See application file for complete search history.

(56) References Cited

U.S. PATENT DOCUMENTS

| | | | |
|---|---|---|---|
| 6,643,652 B2 * | 11/2003 | Helgeson et al. | 1/1 |
| 7,444,346 B2 * | 10/2008 | Bearden et al. | 1/1 |
| 7,551,078 B2 * | 6/2009 | Carlson et al. | 340/539.12 |
| 7,552,057 B2 * | 6/2009 | McGwin, Jr. | 705/1.1 |
| 7,698,405 B2 * | 4/2010 | Brown et al. | 709/223 |
| 7,779,183 B2 * | 8/2010 | Koehler et al. | 710/72 |
| 2004/0088374 A1 * | 5/2004 | Webb et al. | 709/218 |
| 2005/0108057 A1 * | 5/2005 | Cohen et al. | 705/3 |
| 2007/0009161 A1 * | 1/2007 | Hollingsworth | 382/229 |
| 2007/0213598 A1 * | 9/2007 | Howard et al. | 600/300 |
| 2008/0004904 A1 * | 1/2008 | Tran | 705/2 |
| 2008/0034415 A1 * | 2/2008 | Chacko et al. | 726/14 |
| 2008/0146265 A1 * | 6/2008 | Valavi | 455/550.1 |
| 2009/0036750 A1 * | 2/2009 | Weinstein et al. | 600/300 |
| 2009/0058635 A1 * | 3/2009 | LaLonde et al. | 340/539.11 |
| 2009/0063193 A1 * | 3/2009 | Barton et al. | 705/3 |
| 2009/0125332 A1 * | 5/2009 | Martin | 705/3 |
| 2009/0240526 A1 * | 9/2009 | Vesto et al. | 705/3 |

* cited by examiner

*Primary Examiner* — Cheng-Yuan Tseng
(74) *Attorney, Agent, or Firm* — Hanley, Flight & Zimmerman, LLC

(57) ABSTRACT

Certain examples provide systems, apparatus, and methods for adaptive, dynamic medical device connectivity. In an example, a medical device interface system includes a device interface connecting a medical device to a client system and enabling exchange of data between the medical device and the client system, the device interface includes a plug and play detector detecting a connection of the medical device to the device interface and a serial agent gathering information from the medical device via a connection between the medical device and the device interface and selecting an appropriate device driver to operate and interact with the medical device connected to the device interface regardless of a presence or absence of an existing plug and play capability of the medical device.

14 Claims, 13 Drawing Sheets

SYSTEMS, METHODS, AND APPARATUS FOR MEDICAL DEVICE INTERFACE CONNECTIVITY

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND

The present invention generally relates to medical device connectivity. In particular, the present invention relates to systems, apparatus, and methods for adaptive, dynamic medical device interface connectivity.

Clinical environments often involve a variety of medical devices. In a clinical setting such as an intensive care unit (ICU), devices are brought to the bedside when needed and manually set up and configured by clinicians who may have to frequently connect and disconnect the device during normal operation. Thus, clinicians frequently fail to properly configure or set-up such devices.

BRIEF SUMMARY

Certain examples provide systems, apparatus, and methods for adaptive, dynamic medical device connectivity.

In an example, a medical device interface system includes a device interface connecting a medical device to a client system and enabling exchange of data between the medical device and the client system, the device interface includes a plug and play detector detecting a connection of the medical device to the device interface and a serial agent gathering information from the medical device via a connection between the medical device and the device interface and selecting an appropriate device driver to operate and interact with the medical device connected to the device interface regardless of a presence or absence of an existing plug and play capability of the medical device.

In an example, a machine-implemented method for interfacing between a medical device and a clinical information system. The method includes detecting, using a device interface having a serial agent, a presence of a medical device on a network including a clinical information system. The method additionally includes gathering information from the medical device connected to the device interface. The method further includes creating an object representing the medical device, the object including identification and device driver information regarding the medical device. In addition, the method includes searching a device driver repository at the device interface for an object and one or more associated device drivers to represent the medical device. The method includes registering the medical device with the system using the object. The method also includes interacting with the medical device using the one or more associated device drivers to communicate between the medical device and the clinical information system.

In an example, an article of manufacture includes a computer readable storage medium and executable program instructions embodied in the computer readable storage medium that when executed by a programmable system cause the system to perform functions that implement a gaming system arranged to implement a probabilistic game. The functions include a device interface routine connecting a medical device to a client system and enabling exchange of data between the medical device and the client system. The device interface routine includes a plug and play detector detecting a connection of the medical device to the device interface and a serial agent gathering information from the medical device via a connection between the medical device and the device interface and selecting an appropriate device driver to operate and interact with the medical device connected to the device interface regardless of a presence or absence of an existing plug and play capability of the medical device.

Figure 1:
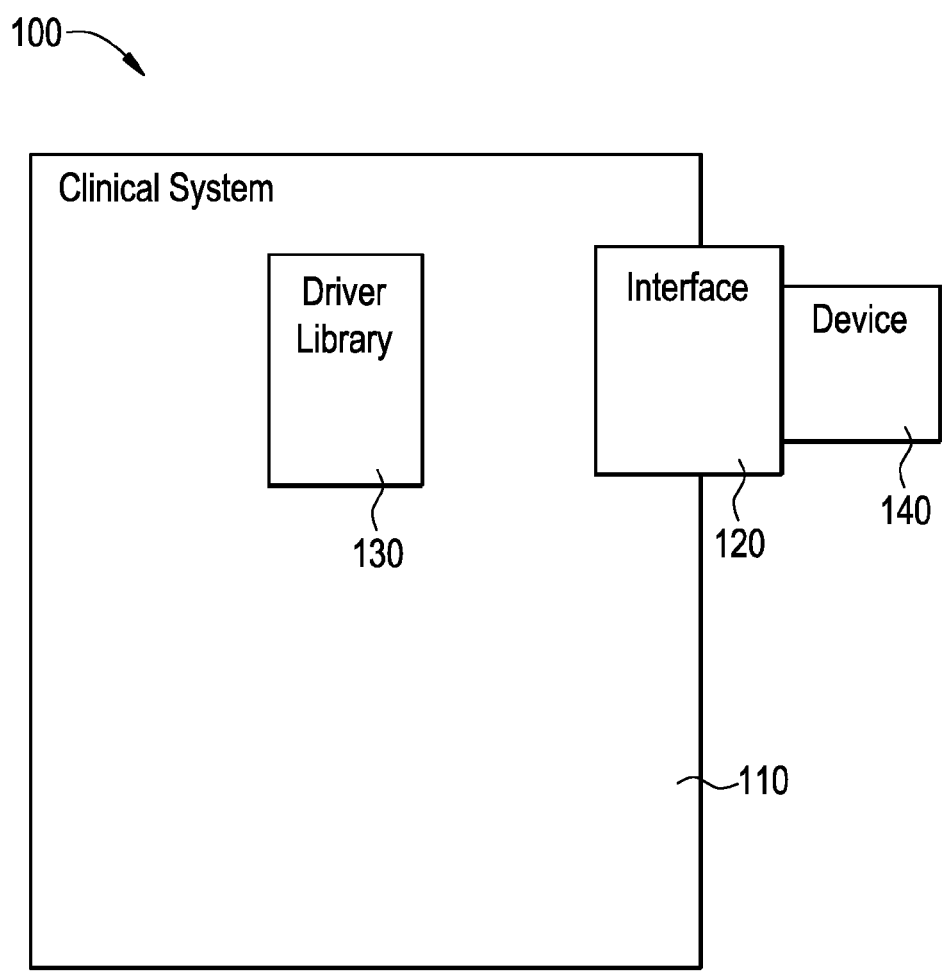
FIG. 1 illustrates an example medical device connectivity system.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements is hereby expressly defined to include a tangible medium such as a memory, DVD, CD, etc. storing the software and/or firmware.

For clinical information systems, medical devices can be used to meet clinical care needs. In a clinical setting such as an intensive care unit (ICU), medical devices are brought to a patient bedside when needed and set up by clinicians who do not put an emphasis or focus on configuration or set up to start/stop a particular device due to frequent connection and disconnection of medical devices.

In an example, a serial agent is capable of executing a plurality of device drivers on a personal computer and/or other computing system or device. A client system that connects to the serial agent can retrieve medical device data in a common format from a medical device with a corresponding device driver. For example, the serial agent converts different device specific formats into one XML-based format.

In operation, for example, a client connected to a serial agent service sends a starting and a stopping command for a specific medical device. The serial agent transforming the device specific communication protocol into a common format then gives the command information to the client system. The serial agent can run any kind of device driver that conforms to the defined interface. Medical devices supported by the serial agent utilize a communication protocol such as an RS-232 port-based communication protocol, a TCP/IP communication protocol, etc. For example, a variety of medical devices such as analyzers, monitors, pumps, ventilators, etc., can be connected to a client system via the serial agent.

Example medical devices, provided in a non-restrictive list for purposes of illustration only, include one or more of a 3M™ CDI 300/400 Blood Gas Analyzer, Abbott Q Vue™/Q2™ CCO Monitor, ALARIS™ Asena, ALARIS™ IVAC P6000/TIVA/P7000, ALARIS™ IVAC TIVA-TCI, Baxter Sat-2™, Baxter VIGILANCE™, BBraun INFUSOMAT™, BBraun INFUSOMAT FM™, BBraun PERFUSOR COMPACT S™, BBraun Perfusor FT™, B-D Modular pump, Bird 8400ST/STi™ Ventilator, Braun DIANET™, Datex-Ohmeda AVANCE™, Datex-Ohmeda CENTIVA™, Datex-Ohmeda DELTATRAC™, Datex-Ohmeda ELVIRA™, Datex-Ohmeda ERICA™, Datex-Ohmeda INOVENT™, Datex-Ohmeda OSCAR™, Datex-Ohmeda SATLITE™, Datex-Ohmeda TONOCAP™, DONI DRV™, Dräger Babylog 8000/8000 SC™, Dräeger EVITA XL™ ventilator, Dräger EVITA™, Dräger EVITA 2™, Dräger EVITA 2 DURA™, Dräger EVITA 4™, Dräger JULIAN™, Dräger SAVINA™, F. Stephan Stephanie, Fresenius-Vial Base A™, GE Datex-Ohmeda S/5™ Patient Monitor, GE Unity AWARE™ Gateway HL7, Hamilton Galileo GOLD™, Hamilton Galileo Ventilator, Ivac 560 (CIM)™, Ivac P-Series, Kone 565, MCM 504/404™ Volumetric Infusion Pump, Newport E150 (Breeze)™ Ventilator, Newport E200 (Wave)™ Ventilator, Philips Information Center HL7, Philips IntelliVue MP40/50/60/70/90™, Pulsion PICCO MONITOR™, Puritan-Bennett 7200™, Puritan-Bennett 7200 VENTILATOR™ (Liter version), Puritan-Bennett 840 VENTILATOR™, Puritan-Bennett 7200 VENTILATOR™ (ml version), Puritan-Bennett 840 VENTILATOR™, Siemens SC9000™, Siemens SERVO 300™, Siemens SERVO 900™, Siemens SERVOI™, Siemens SIRECUST™, SLE 2000™ High Frequency Ventilator, Solar 8000i™, Solar 8000M™, Solar 9500™, TBird AVS III™, TERUMO™ infusion pump, TERUMO™ syringe pump, TOP-3300™ Infusion Pump, etc.

Using a serial converter, such as a universal serial bus (USB) serial converter to uniquely identify the device for serial agent clinical information system platform software. The serial agent platform transforms medical device data in a plug and play manner to enable use of the medical device by the clinical information system and/or transfer of information between the medical device and the clinical information system, for example. Plug and play functionality provides improved bedside medical care usage of connected medical device(s). With an adaptively connected medical device, a hospital clinician does not need to pay attention to manually configure a connected medical device but can instead simply plug-in a device when it is needed. Furthermore, a clinician can disconnect a device without paying additional attention to software configuration for the device and/or for the clinical information system. In an example, the same serial agent device driver can be used for a plurality of "plug-and-play" enabled devices as well as non plug-and-play devices, such as connectable medical devices using the RS-232 data communication protocol, without additional modification of existing device drivers and/or additional hardware support (such as a concentrator box traditionally used to ensure connectivity). For example, using a pre-configured USB RS-232 converter to uniquely identifying a medical device (e.g., referred to as a device identifier), the medical device can be initiated and used with common device driver that is used for both plug and play and non plug and play devices. Medical devices without plug and play support can be transformed into plug and play devices within the serial agent system, for example.

As shown, for example, in FIG. 1, a medical device connectivity system 100 includes a clinical system 110, a device interface 120, a driver library 130, and a medical device 140. In an example, a device interface 120, such as the CENTRICITY® Device Interface sold by GE Healthcare, provides a framework to execute device drivers that gather information from one or more connected medical devices 140. The framework includes a driver library 130 including device drivers for a plurality of medical devices 140. From the library 130 can be found a plurality of device drivers for different medical devices.

Using the device interface 120, discovery of a connected device 140 (e.g., hardware, firmware and/or software) is facilitated without manual device configuration or user intervention (e.g., plug and play connectivity). Plug and play connectivity can be facilitated using universal serial bus (USB), FIREWIRE™, and/or other hot plug/hot swap connection, for example. Thus, device connectivity can be developed in the device interface 120 to enable dynamic, adaptive connectivity with the interface 120 using a converter such as a Future Technology Devices International (FTDI) USB serial converter, for example. Information can be gathered from and/or transmitted to a medical device 140 via an interface 120, such as an interface including a USB connector/converter, to allow the device 140 to communicate with one or more clinical systems 110, such as a hospital information system (HIS), radiology information system (RIS), clinical information system (CIS), cardiovascular information system (CVIS), picture archiving and communication systems (PACS), library information system (LIS), electronic medical record (EMR), electronic health record (EHR), personal health record (PHR), and/or imaging system, for example. Using the interface 120 and driver library 130, the system 100 detects the medical device 140, such as a USB-enabled medical device, being connected or disconnected from the clinical system 110. Using the interface 120 and driver library 130, the system 100 supports a plug and play communication mode, such as a USB communication mode, to gather data from the medical device 140.

Figure 2:
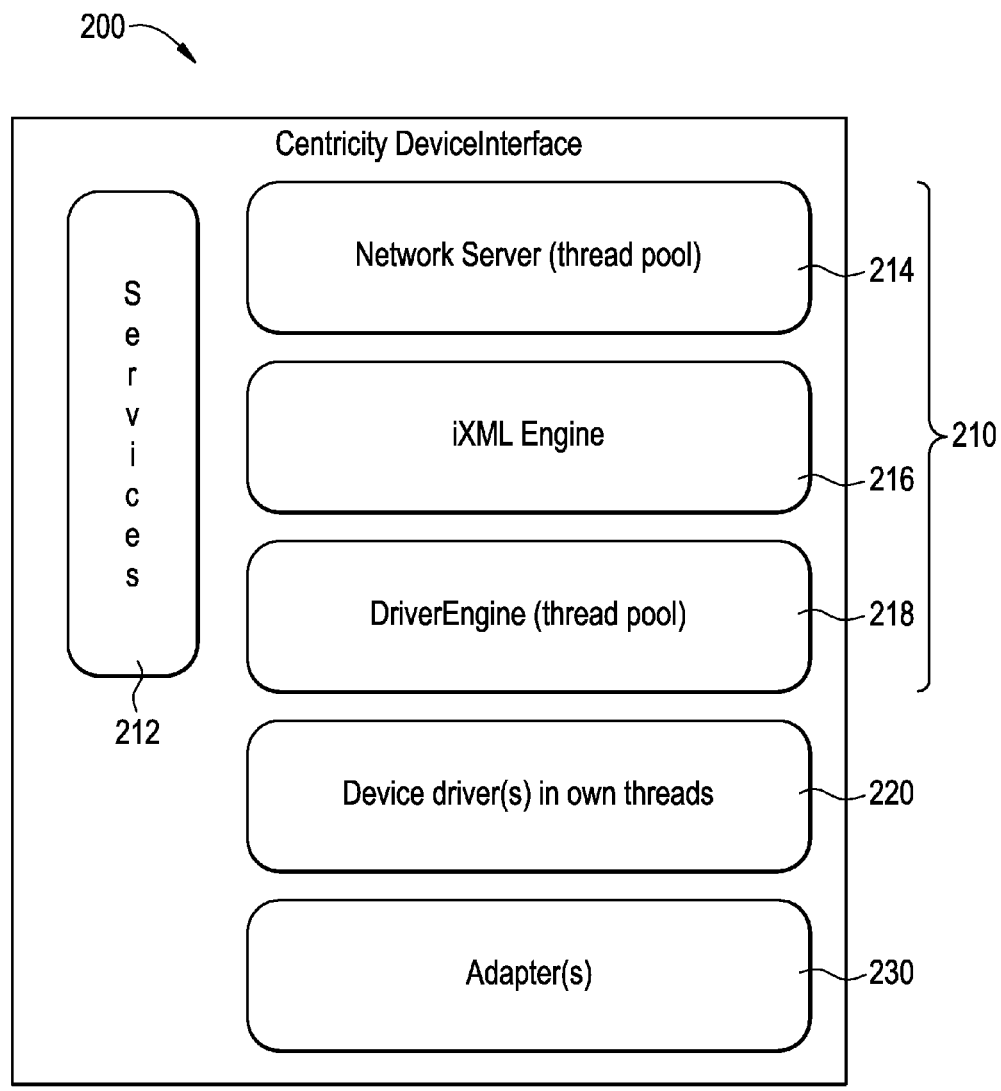
FIG. 2 depicts an example device interface architecture.

FIG. 2 depicts an example device interface architecture 200 that can be implemented in an interface such as the device interface 120 described above. The device interface architecture 200 includes a core 210, one or more device driver threads 220, and one or more adapters 230, for example. The core 210 is layered into one common service layer 212 and three special purpose layers: a network server 214, an interface eXtensible Markup Language (iXML) Engine 216, and a Driver Engine 218.

Each layer performs its own set of related tasks. For example, the Network Server 214 communicates with a client system, such as the clinical system 110, over a data communication interface, such as a TCP/IP interface, using data messages, such as iXML (interface eXtensible Markup Language) messages which structures the data used by the device interface. The iXML Engine 214 parses inbound messages and builds outbound iXML messages, for example. The Driver Engine 216 manages the device drivers 220 and forms a pool of threads for device driver execution. The device drivers 220 communicate with the one or more connected medical devices and translate data from medical device(s) into device interface internal format. Adapter(s) 230 provide a communication channel (e.g. serial or TCP/IP) to the medical device.

In an example, a client system 110 can develop one or more device drivers using an interface 120 protocol adaptor. The driver(s) can be added to the driver library 130 and used to configure driver information for the interface 120.

Figure 3:
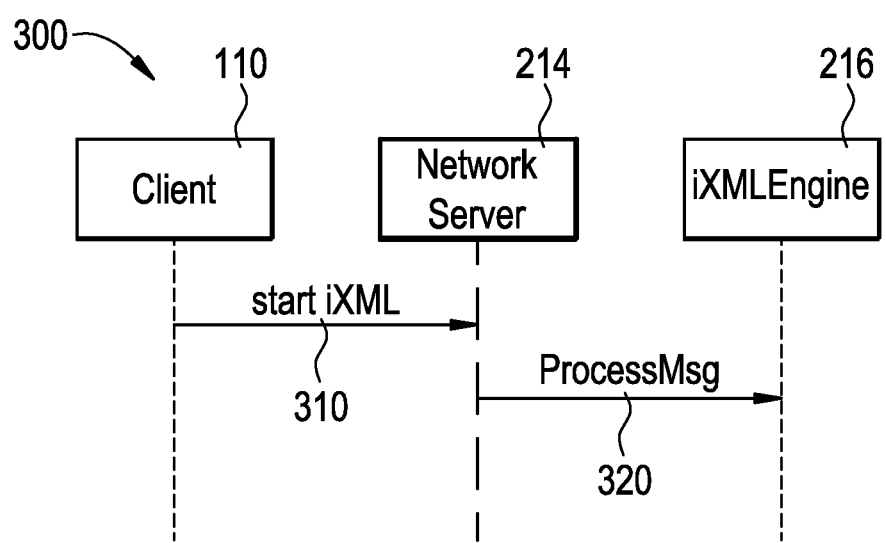
FIG. 3 depicts an example client-server data flow.

As shown, for example, in the data flow 300 of FIG. 3, a client 110 requests medical data by sending an iXML start message 310 to the network server 214. The network server 214 receives the iXML start message 310 and generates a message to be processed 320 by the iXML engine 216. The message to be processed 320 is used by the iXML engine 216 to create a session to select a device driver to run the medical device.

Figure 4:
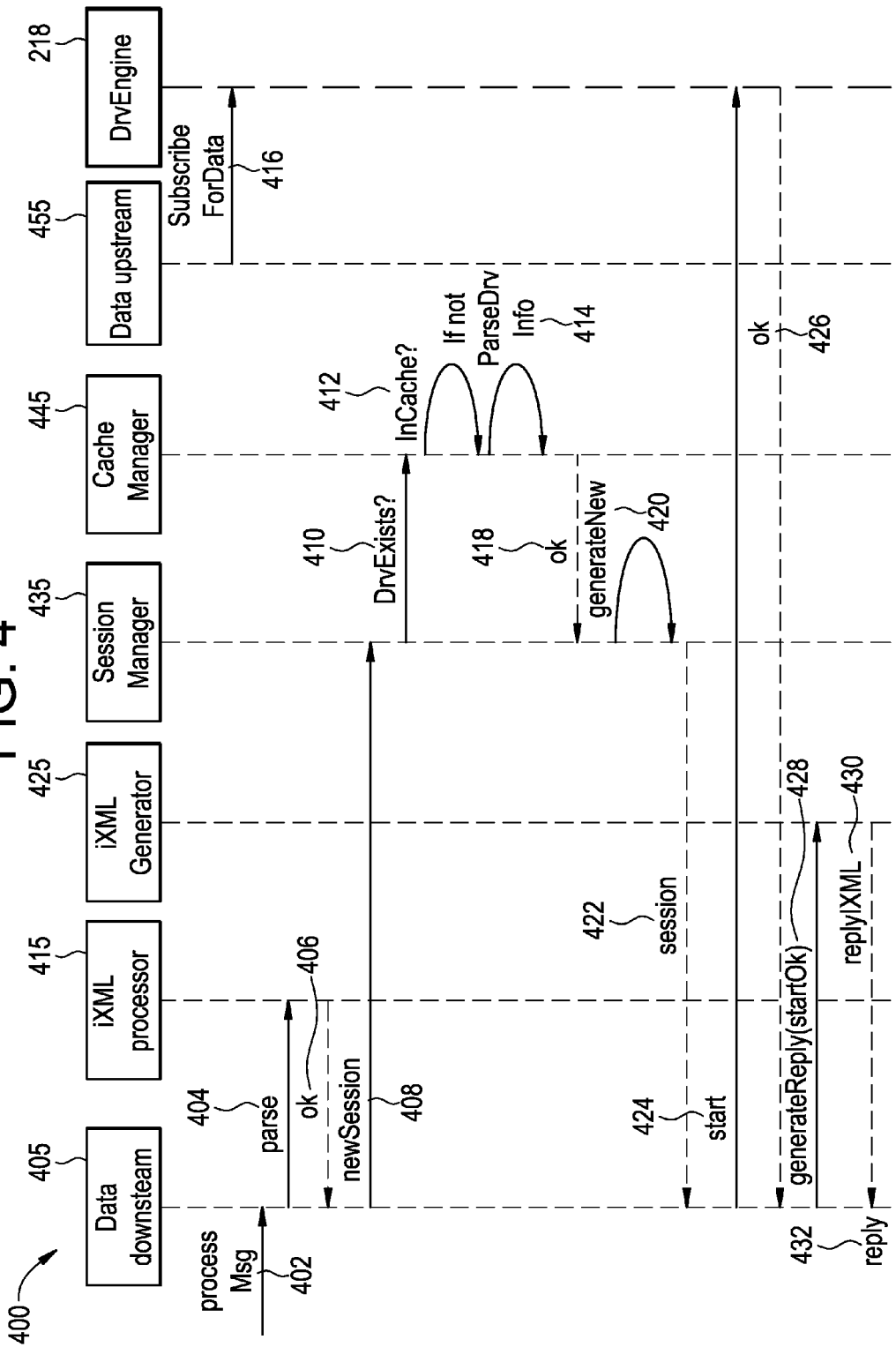
FIG. 4 illustrates an example data flow to initiate a device session to select a device driver and communicate with and/or otherwise execute a connected medical device.

FIG. 4 illustrates an example data flow 400 to start a device session to select a device driver and communicate with and/or otherwise execute a connected non plug and play enabled medical device via the iXML engine 216. The device interface reads a configuration file and begins connectivity checking, such as USB connectivity checking, in a device initialization phase. The interface starts or stops executing a device driver when it detects a USB device being connected or disconnected from the interface (e.g., the device interface 120), for example. The data sequence 400 illustrates a non-plug and play program sequence in, for example, USB mode, to start a device session in the iXML engine 216.

As shown in FIG. 4, a process message 402 is received by the iXML engine 216. The process message 402 is received by a data downstream module 405 of the iXML engine 216. The data downstream module 405 instructs the iXML processor 415 via a parse message 404 to which the iXML processor 415 responds with an acknowledgement 406. After receiving an acknowledgement 406 from the iXML processor 415, the data downstream module 405 generates a new session message 408 which is sent to a session manager 435.

The session manager 435 creates a new session and queries a cache manager 445 to determine whether a driver for the connected medical device exists 410. If the driver is in the cache 412, then that information is used to subscribe for data 416 with the driver engine 218 via the data upstream module 455. If the driver is not found in the cache, then driver information is parsed 414 to determine an appropriate driver for subscription at the driver engine 218. After a driver is identified and selected, an acknowledgement 418 is sent from the cache manager 445 to the session manager 435 to generate a new session 420. The new session 422 is provided to the data downstream module 405.

After receiving the new session information 422, the data downstream module 405 generates a start message 424 for the driver engine 218. The driver engine 218 responds with an acknowledgement 426 to the data downstream 405. A reply 428 is generated okaying the start for an iXML generator 425. The iXML generator 425 generates a reply iXML message 430, which is provided by the data downstream 405 as a reply 432 to the network server 214.

Figure 5:
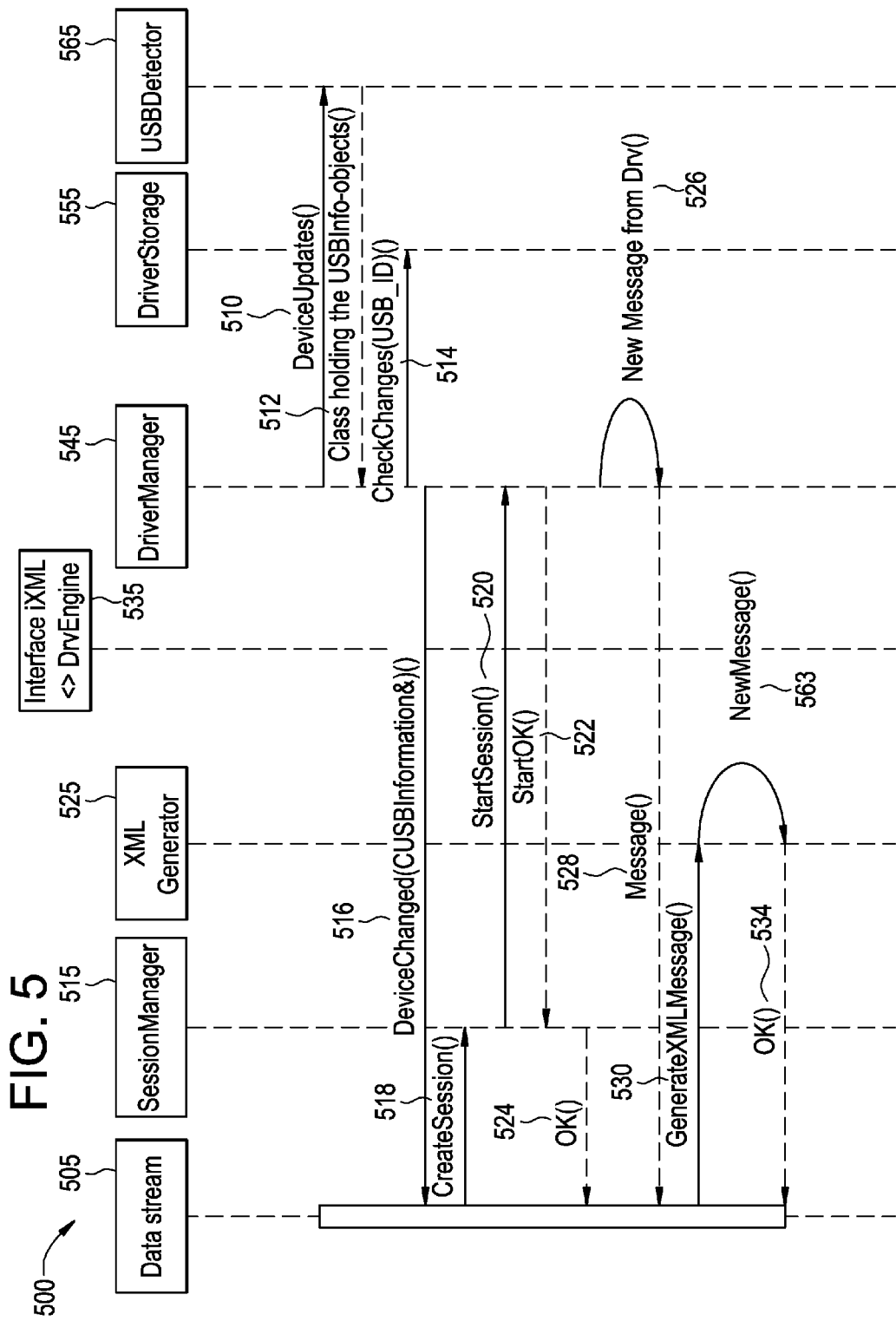
FIG. 5 illustrates an example data sequence to start a device session.

In FIG. 5, the data sequence 500 to start a plug and play enabled device session is modified to initialize, for example, a USB mode and include additional threads to detect a USB device connection and perform a watchdog function for such a thread. Additionally, a session identifier is created for internal interface use, and a virtual communication port is created for the USB serial medical device. While FIG. 4 is shown as a non-plug and play program sequence, and FIG. 5 is shown as a plug and play program sequence, both types of connectivity can co-exist in the same system.

FIG. 5 illustrates an example interaction and data flow between components of the iXML engine 216 (e.g., data stream 505, session manager 515, XML generator 525) and the driver engine 218 (e.g., driver manager 545, driver storage 555, USB detector 565) via an iXML/Driver engine interface 535. In the data flow 500 of FIG. 5, for example, a driver manager 545 generates a device update 510 and transmits the device update 510 to a USB detector 565. In response, the USB detector 565 generates a class holding one or more USB information objects 512. The driver manager 545 receives the USB information object(s) and determines whether changes have been made to the USB information by transmitting a change message 514, including a USB identifier, to a driver storage 555. A device changed message 516 including USB information is transmitted from the driver manager 545 back to the data stream 505.

In response to the USB device information 516, a create session message 518 is generated from the data stream 505. The session manager 515 receives the create session message 518 and generates a start session message 520 for the driver manager 545. The session manager 515 can create a session identifier for internal use and reference. The driver manager 545 responds with an acknowledgement 522. The session manager 515 similarly responds with an acknowledgement 524 to the data stream 505.

The driver manager 545 generates a new driver message 526 and transmits a message 528 to the data stream 505. In response, the data stream 505 sends a request to generate an XML message 530 to an XML generator 525. The XML generator 525 generates a new message 532 and acknowledges the generation of the new message 534 to the data stream 505.

Using the data sequence 500 of FIG. 5, a processing thread for detecting USB device connection is created in the device interface 120. An event caused by a change in system registry information leads to the device interface 120 to scan system device information and detect the USB (and/or other data)

connection. The USB detector 565 is also responsible for checking the device information in memory, such as an electronically erasable programmable read-only memory (EEPROM), erasable programmable read-only memory (EPROM), other programmable read-only memory (PROM), random access memory (RAM), flash memory, hard disk drive, etc. The USB detector 565 notifies the session manager 515 to start/stop a session when it detects a USB device 140 connected/disconnected to the interface 120. Additionally, a watch dog thread running in the background on the driver engine can be used to launch the USB detector thread In an example, the device interface 120, 200 includes a USB serial converter having a memory, such as an EEPROM and/or other data storage such as the memory discussed above. The USB converter EEPROM is configured to adapt a medical device 140 for use by a clinical system 110. Configuration information for the USB converter to accommodate one or more medical devices 110 via the device interface 120 can include a unique device identifier for each device instance, a device vendor identifier, a product identifier, a device name, a driver file name, etc. If the device identifier from the EEPROM is in conflict with other device(s) connected in the system, the device interface sends an iXML message to the client to specify that a second device having the same device identifier as a first device and the device interface is not able to communicate with the second device, for example.

In an example, a configuration tool can be provided for the USB converter. The configuration tool parses basic USB information and device information specific to the interface 120, 200. USB basic information can include vendor identifier, product identifier, serial number, enable USB serial number, etc. Interface specific information can include device identifier, device name, and device file (e.g., dynamic link library (DLL)) name, etc. The configuration tool can erase interface specific device information, for example. The configuration tool can be used to upload interface device specific information to the USB EEPROM based on user input, for example. For a USB device connected to the device interface, the USB serial number is enabled. The configuration tool can provide a way to enable the USB serial number.

A USB device object is created to detect USB converter connection and/or disconnection. To create the device object, device information such as vendor identifier, product identifier, device serial number, and virtual communication port number is retrieved from an operating system registry. An application programming interface can be used to obtain device identifier, device, and device driver file name from the serial converter. Using USB converter serial number, the virtual communication port and device name can be associated.

Figure 6:
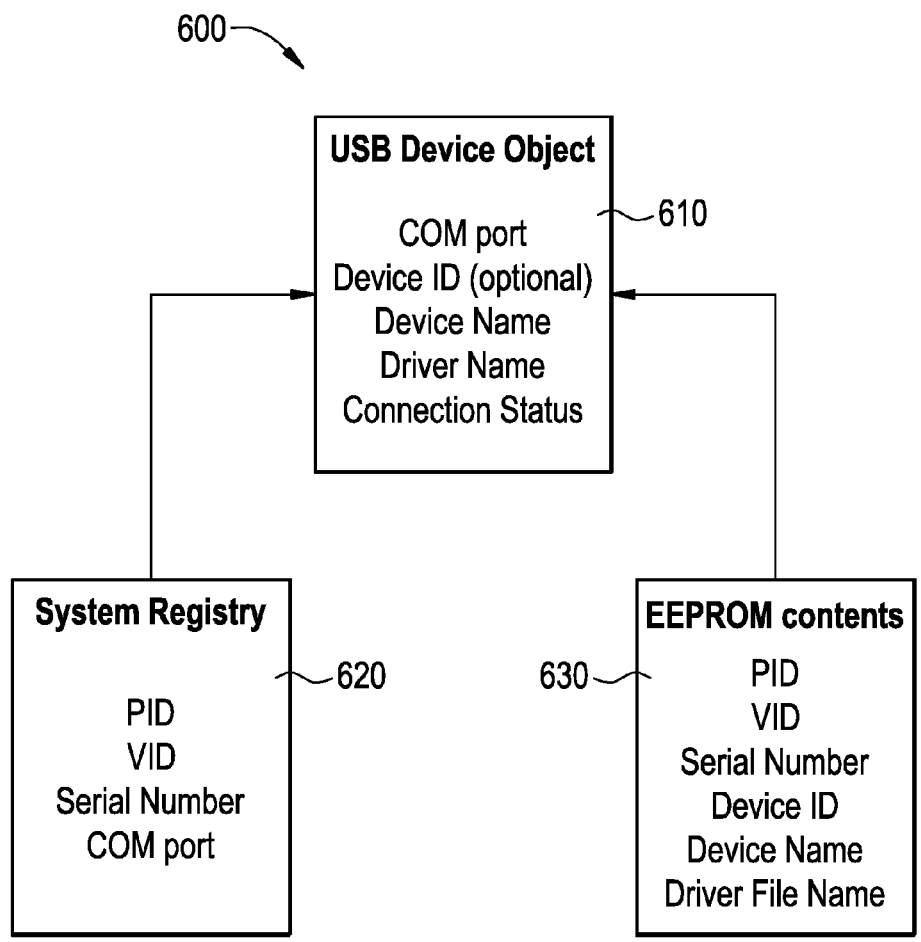
FIG. 6 illustrates an example USB device object created via the device interface using information from a system registry and a converter EEPROM.

As illustrated, for example, in FIG. 6, a USB device object 610 can be created via the device interface using information from a system registry 620 and a converter EEPROM 630. Information such as product identifier, vendor identifier, serial number, and communication port are transferred from the system registry 620 to the device object 610. Information such as product identifier, vendor identifier, serial number, device identifier, device name, and driver file name are transferred from the EEPROM 630 to the device object 610. The device object 610 stores information such as communication port, device identifier, device name, driver name, and connection status for use in communicating with the connected device, for example.

In an example, USB and/or other connection detection can be handled using a plurality of (e.g., four) states in a state machine. Example states include invalid, new connection, no change, and removed connection. For example, when a USB device is connected but a virtual communication port is not found or device information read from an EEPROM has failed, the device interface notifies the client by sending out an XML message when the USB connection is in the invalid state. When a USB converter is connected to the system, the device interface initiates a new session in the new connection state. In the no change state, the USB connection is maintained and the device session is working. The device driver is continuing to execute and collect data from the connected medical device in this state. When a USB converter is unplugged or otherwise disconnected, a USB session is removed in the removed connection state, for example.

Figure 7:
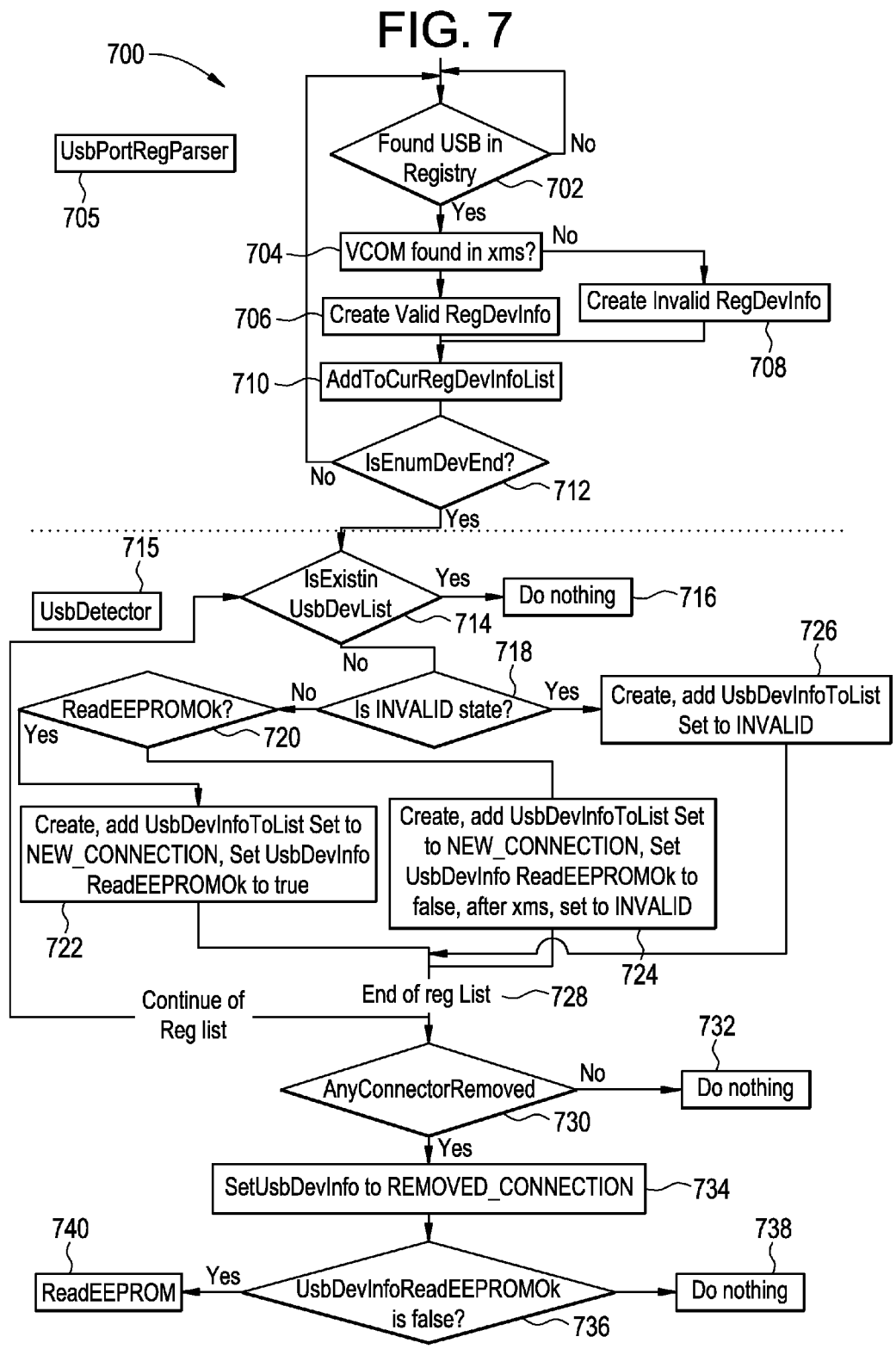
FIG. 7 illustrates a flow diagram for an example method for detecting a USB physical connection with a medical device via a device interface including a USB port registry parser and a USB detector.

FIG. 7 illustrates a flow diagram for an example method 700 for detecting a USB physical connection with a medical device via a device interface including a USB port registry parser 705 and a USB detector 715. At 702, a registry is reviewed to identify a connected USB device. If the USB device is not found, the process iterates to continue to search for or create a registry entry for the device. If a registry entry for the device is found, then, at 704, system messaging (XMS) is searched for a virtual communication port (VCOM). If a VCOM is found for the device, then valid registry device information is created at 706. If a VCOM is not found, then an invalid registry device information is created at 708. The valid or invalid registry device information is added to a current registry device information list at 71 0.

At 712, a list of connected device(s) is checked to determine whether the end of the list has been reached. If not, the process loops back to review the registry at 702. If so, the process passes to the USB detector 705 to determine whether, at 714, the USB device exists in a USB device list for the system. If so, at 716, then nothing further is done. If not, then, at 718, device interface state is examined to determine whether the state is set to invalid. If the state is not invalid, then, at 720, the EEPROM is read. If the EEPROM is successfully read, then, at 722, the USB device is added to the USB device list. The state is set to new connection and the EEPROM read for the UESB device information is noted. If the EEPROM was not successful read, then, at 724, the USB device is added to the USB device list and the state is set to new connection. However, the USB device information read EEPROM value is set to false and, after XMS, state is set to invalid. At 726, if the state is invalid at 720, the USB device information is added to the list and interface state is set to invalid.

At 728, if the process has not reached the end of the device registration list, the process loops back to reviewing the list at 714. If the process has reached the end of the registration list, then at 730, USB connectors are checked to determine whether a connector has been removed. If not, then, at 732, nothing is done. If so, then, at 734, USB device information for that device is set to a state of removed connection. At 736, if USB device information read EEPROM has been set to false, then the EEPROM is read at 740. If not, then nothing is done at 738.

Figure 8:
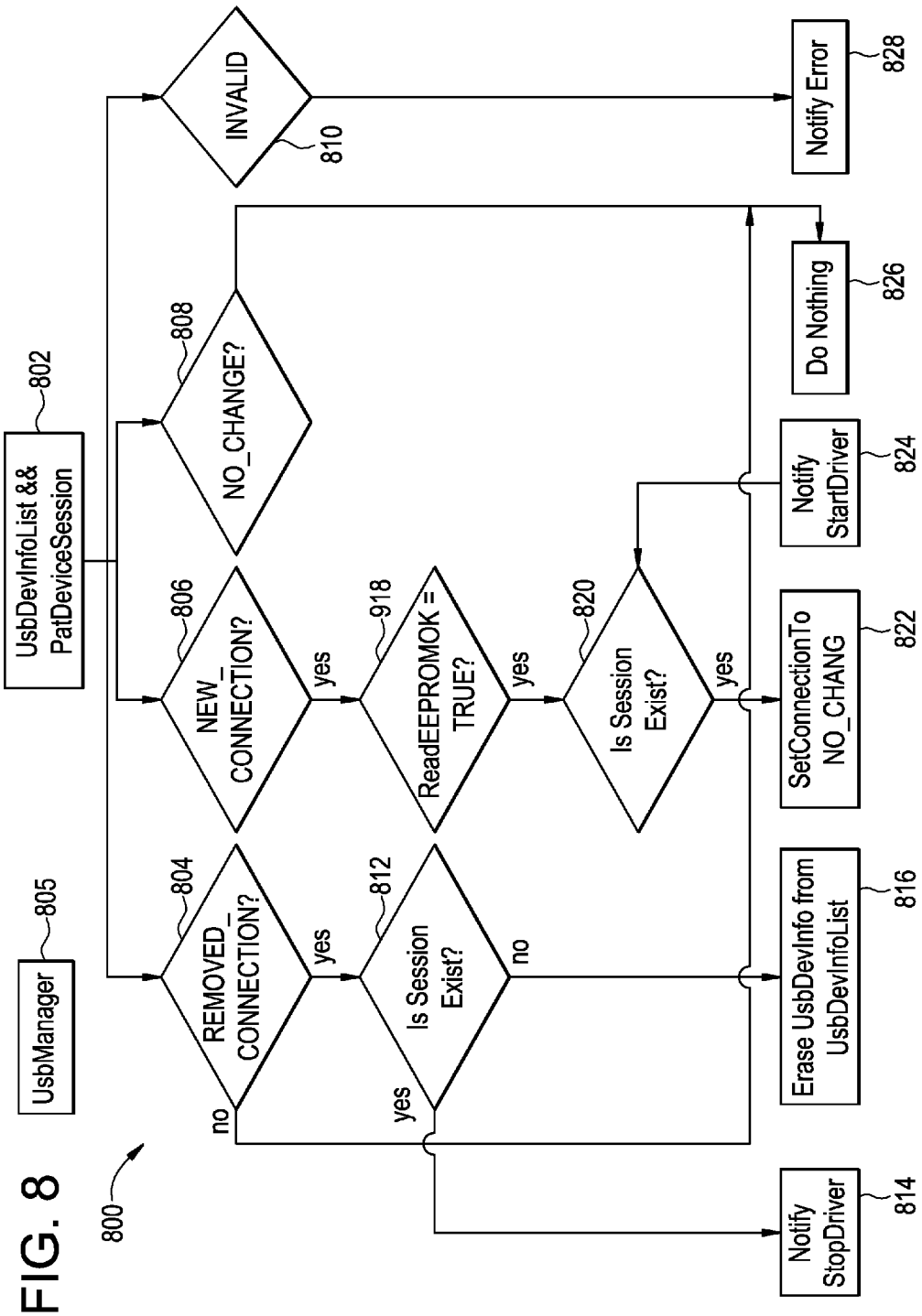
FIG. 8 depicts another example sequence for changing USB connection status executed by a USB manager.

FIG. 8 depicts another example sequence 800 for changing USB connection status executed by a USB manager 805. At 802, a USB device information list and a device session are opened. At 804, an interface system state is examined to determine whether the state is currently set to a removed connection. If no, then nothing is done at 826. If the state is set to removed connection, then, at 812, existence of a device session is examined. If a session exists, then, at 814, a stop driver is notified to end the session and stop the device driver for the removed device. If a session does not exist, then, at 816, the USB device information for the removed device is erased from the USB device information list.

At 806, the USB manager 805 determines if the interface is in a new connection state. If yes, then the read EEPROM okay value is compared to true. If the EEPROM was read okay, then, at 820, existence of a device session is determined. If no device session exists, then, at 824, a start driver is notified to start a device driver for the connected device. If a device session exists, then, at 822, the device connection state is set to "no change." At 808, if the connection state is no change, then, at 826, nothing is done. At 810, if the state is set to invalid, then, at 828, an error notification is generated.

Figure 9:
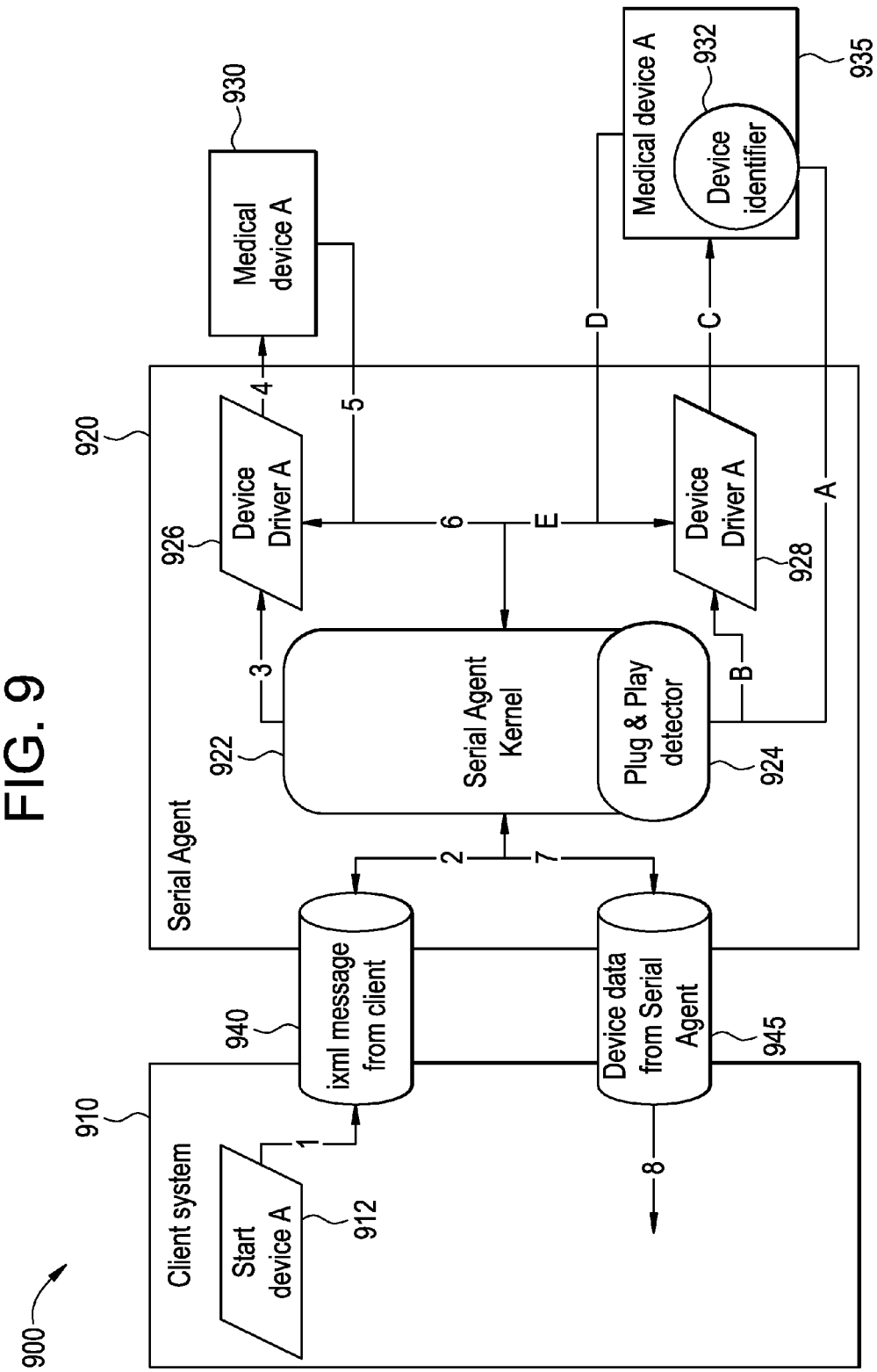
FIG. 9 illustrates an example client-agent system for adaptive connection with one or more medical devices.

FIG. 9 illustrates an example client-agent system 900 for adaptive connection with one or more medical devices. The system 900 includes a client system 910, a serial agent 920, and a plurality of medical devices 930, 935. The client system 910 includes a start device module 912, for example. The serial agent 920 includes a serial agent kernel 922 with a plug and play detector 924 and a plurality of device drivers 926, 928, for example. The medical devices 930, 935 include a device identifier 932, for example.

In operation, the start device module 912 of the client system 910 sends a message 940, such as an iXML message, from the client system 910 to the serial agent kernel 922 of the serial agent 920. In response to the message 940, the kernel 922 initiates an appropriate device driver 926 to communicate with the medical device 930. The device 930 responds to the device driver 926 and to the serial agent kernel 922. The serial agent kernel 922 in turn provides device data 945 to the client system 910.

The plug and play detector 924 of the serial agent kernel 922 can interact with a medical device 935 to obtain information from the device identifier 932 for the medical device 935. Using the device identification information, the plug and play detector 924 can select an appropriate device driver 928 for the device 935. The device 935 communicates with the device driver 935 and the serial agent kernel 922.

As illustrated, for example in FIG. 9, the client system 910 is a Clinical Information System that connects to the serial agent 920 with a TCP/IP-socket. The client system 910 and serial agent 920 communicate using an XML-based protocol. The client system 910 asks the serial agent 920 to start a device driver(s) 926, 928. Alternatively or in addition, the serial agent 920 can start and/or stop a device without a command message from the client system 910 (e.g., for a plug and play device). After the driver 926, 928 has been started, the driver 926, 928 collects data from the medical device 930, 935 at configured intervals and passes the data to the serial agent kernel 922. The kernel 922 transforms the data into the XML-based protocol and provides the data to the client system 910. The data flows between the serial agent 920 and client system 910. The system 900 runs the same device 930, 935 with same driver 926, 928 in a plug & play manner by adding a device identifier 932 in the system. The serial agent kernel 922 builds in a plug and play device detector 924 that collects device information from the device identifier 932. The serial agent kernel 922 starts the device 930, 935 accordingly. The manual start/stop a device and plug and play data flows can co-exist in the same system 900 simultaneously, for example.

Thus, a variety of plug and play and non-plug and play devices can be adapted to function with a client clinical system using a device interface/converter to help facilitate ease of device usage for medical care. A USB serial converter, for example, can be used to uniquely identify the device for a serial agent clinical information system platform via hardware, software, and/or firmware. The serial agent platform is then enabled to transform device data in a plug and play manner.

Figure 10:
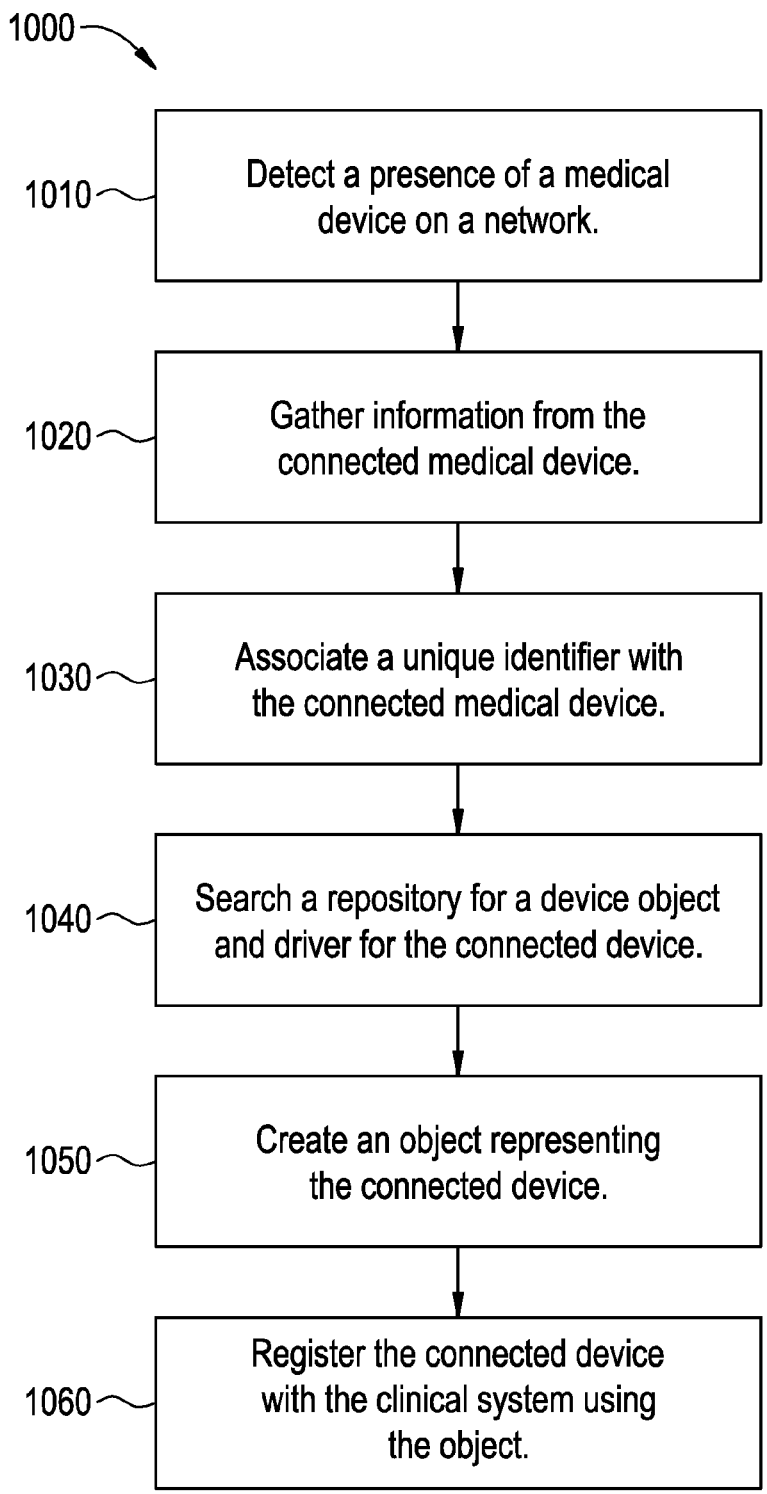
FIG. 10 illustrates a flow diagram for an example method for medical device identification and communication with a client system.

FIG. 10 illustrates a flow diagram for an example method 1000 for medical device identification and communication with a client system. At 1010, a presence of a medical device is detected on a network including a clinical information system. For example, an interface detects connection of a ventilator to the interface USB port. At 1020, information is gathered from the medical device connected to the network. For example, device identification information and/or driver information can be provided to the interface. At 1030, a unique identifier is associated with the medical device by which the clinical information system can reference the medical device. For example, using a USB serial converter in the interface, an identifier is retrieved from the device and assigned in a session for the connected device to facilitate interaction with the device (e.g., data gathering, control, etc.). At 1040, a repository is searched for an object and associated device driver(s) to represent the medical device. At 1050, an object is created representing the medical device. At 1060, the medical device is registered with the system using the object. The client system can then interact with the connected medical device (e.g., through data gathering, command transmission, etc.).

Figure 11:
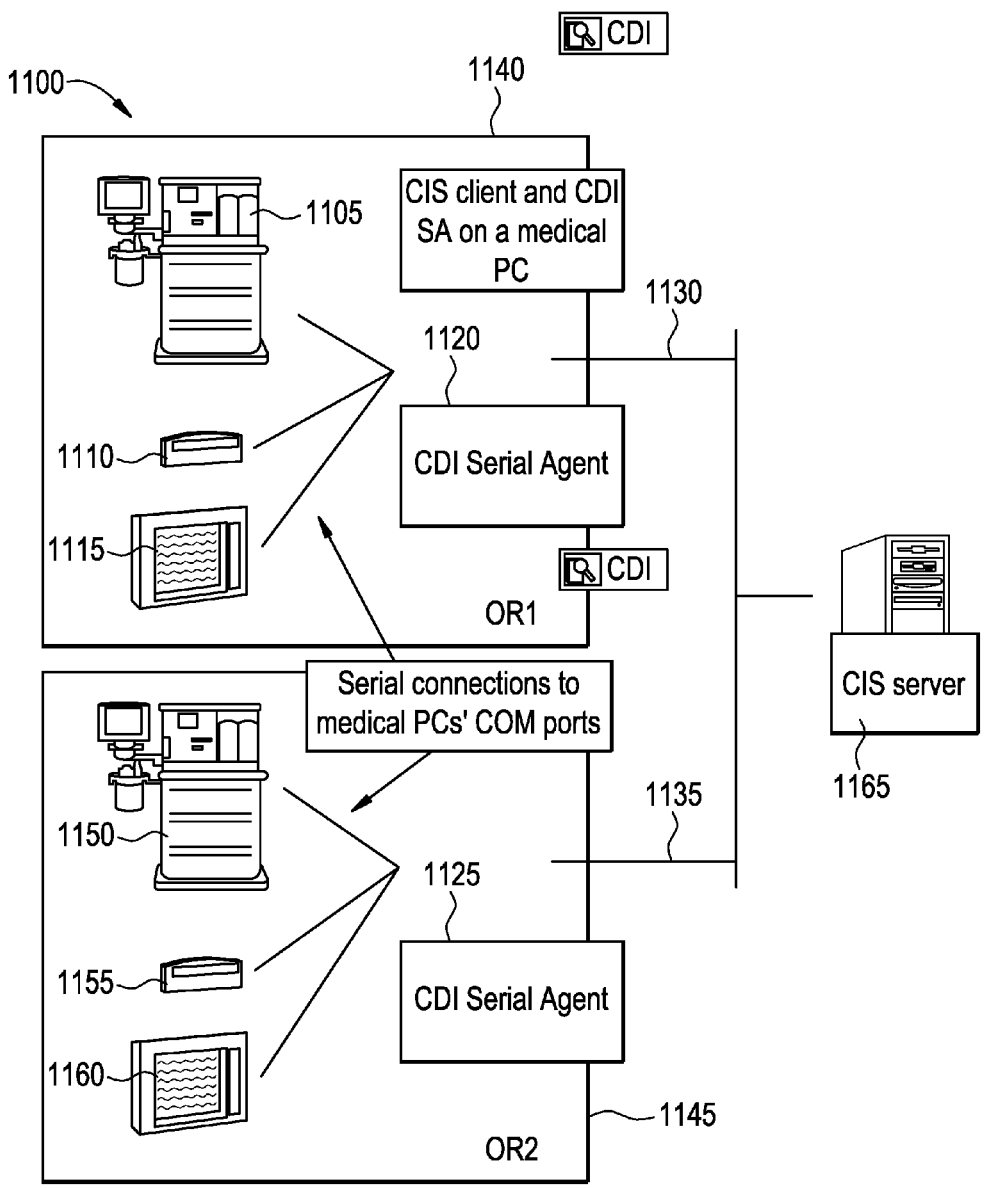
FIG. 11 illustrates an example system in which medical devices are connected to a clinical information system using a device interface.
Figure 12:
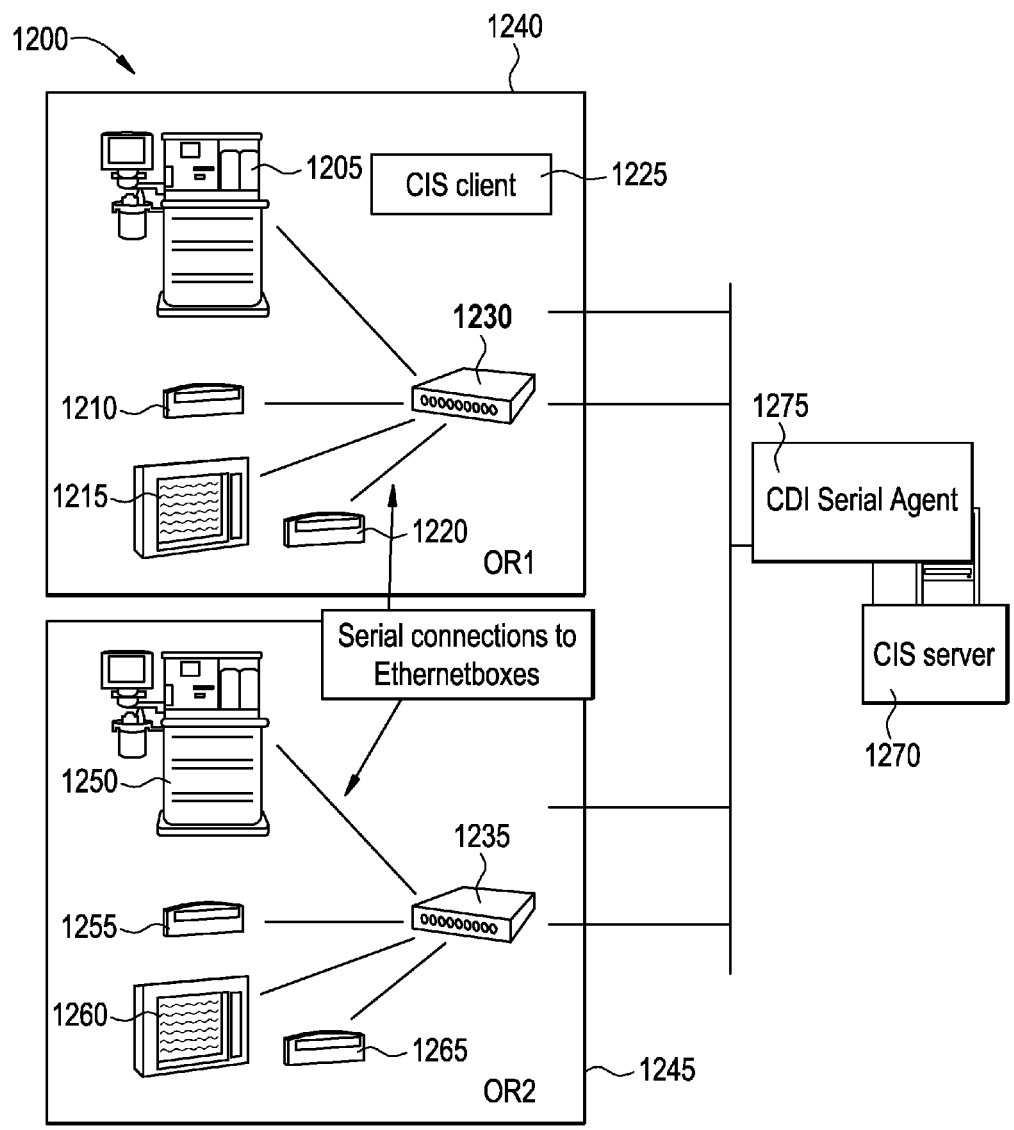
FIG. 12 illustrates an example system in which medical devices are connected to a clinical information system using a device interface.

FIGS. 11 and 12 illustrate example systems 1100, 1200 in which medical devices are connected to a clinical information system using a device interface. In FIG. 11, devices such as a mobile cart 1105, electronic scale 1110, and display 1115 communicate with a device interface serial agent 1120 on a computer 1130 housing the serial agent and a clinical information system client 1120. The devices 1105, 1110, 1115 communicate with the computer via serial connections to the communication (COM) ports of the computer 1130. The devices 1105, 1110, 1115 and computer 1130 are located in a first operating room 1140. A second operating room 1145 can include a second computer 135 with a serial agent 1125 communicating with additional devices 1150, 1155, 1160. The computers 1130, 1135 communicate with a clinical information system server 1165.

In FIG. 12, one or more devices 1205, 1210, 1215, 1220 communicate with a router box 1230 associated with a clinical information system client 1225 via serial connection in a first operating room 1240. Similarly, one or more devices 1250, 1255, 1260, 1265 communicate with a router box 1235 in a second operating room 1245. The router boxes 1230, 1235 communicate with a clinical information system server 1270 having a device interface serial agent 1275 such that control is more centralized than distributed among multiple serial agents as in FIG. 11.

Figure 13:
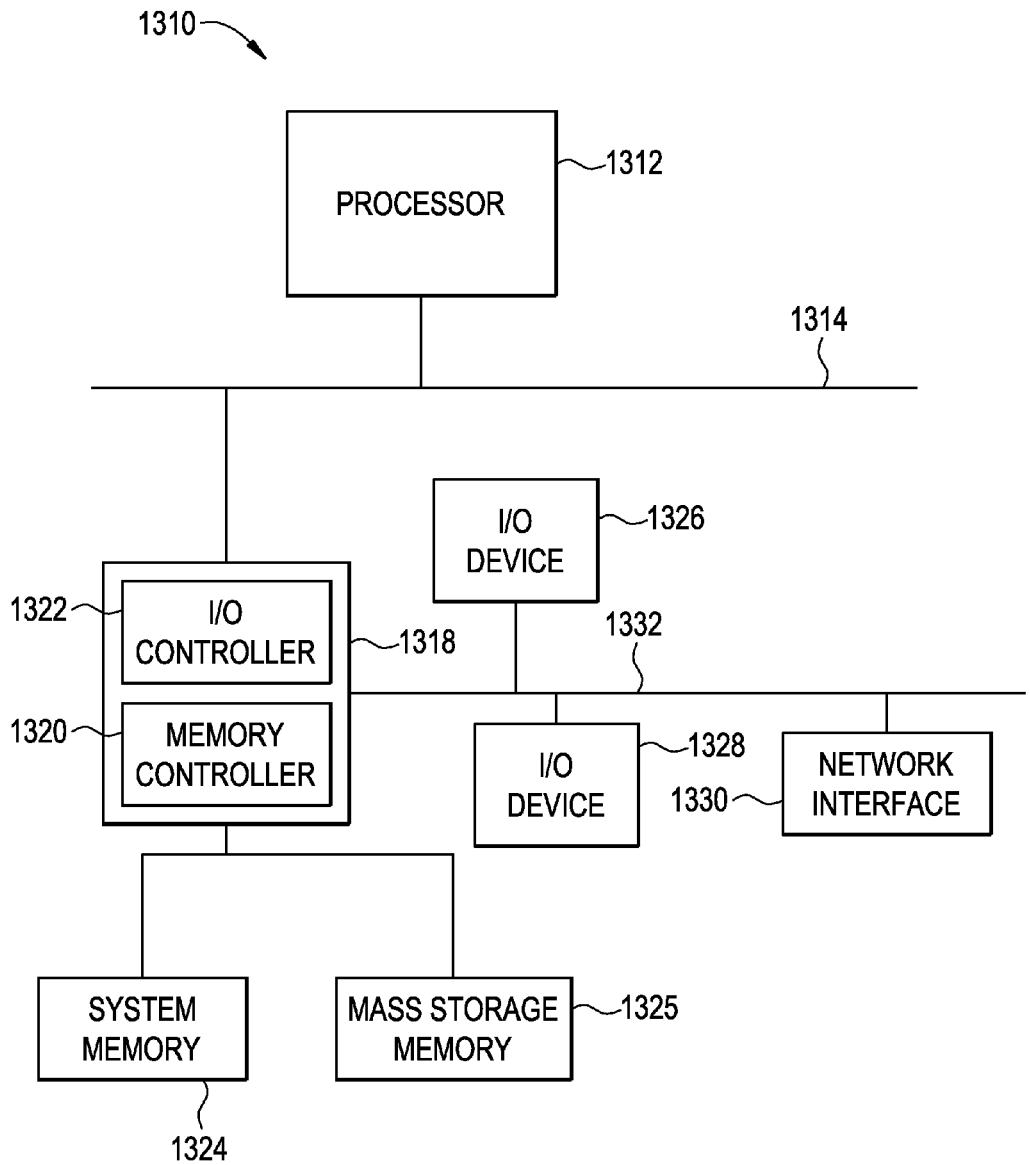
FIG. 13 is a block diagram of an example processor system that may be used to implement systems, apparatus, and methods described herein.

FIG. 13 is a block diagram of an example processor system 1310 that may be used to implement systems, apparatus, and methods described herein. As shown in FIG. 13, the processor system 1310 includes a processor 1312 that is coupled to an interconnection bus 13 14. The processor 1312 may be any suitable processor, processing unit, or microprocessor, for example. Although not shown in FIG. 13, the system 1310 may be a multi-processor system and, thus, may include one or more additional processors that are identical or similar to the processor 1312 and that are communicatively coupled to the interconnection bus 1314.

The processor 1312 of FIG. 13 is coupled to a chipset 1318, which includes a memory controller 1320 and an input/output ("I/O") controller 1422. As is well known, a chipset typically provides I/O and memory management functions as well as a plurality of general purpose and/or special purpose registers, timers, etc. that are accessible or used by one or more processors coupled to the chipset 1318. The memory controller 1320 performs functions that enable the processor 1312 (or processors if there are multiple processors) to access a system memory 1324 and a mass storage memory 1325.

The system memory 1324 may include any desired type of volatile and/or non-volatile memory such as, for example, static random access memory (SRAM), dynamic random access memory (DRAM), flash memory, read-only memory (ROM), etc. The mass storage memory 1425 may include any desired type of mass storage device including hard disk drives, optical drives, tape storage devices, etc.

The I/O controller 1322 performs functions that enable the processor 1312 to communicate with peripheral input/output ("I/O") devices 1326 and 1328 and a network interface 1330 via an I/O bus 1332. The I/O devices 1326 and 1328 may be any desired type of I/O device such as, for example, a keyboard, a video display or monitor, a mouse, etc. The network interface 1330 may be, for example, an Ethernet device, an asynchronous transfer mode ("ATM") device, an 802.11 device, a DSL modem, a cable modem, a cellular modem, etc. that enables the processor system 1310 to communicate with another processor system.

While the memory controller 1320 and the I/O controller 1322 are depicted in FIG. 13 as separate blocks within the chipset 1318, the functions performed by these blocks may be integrated within a single semiconductor circuit or may be implemented using two or more separate integrated circuits.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine accessible or readable medium and executable by, for example, a processor system (e.g., the example processor system 1410 of FIG. 14). When any of the appended claims are read to cover a purely software and/or firmware implementation, at least one of the components is hereby expressly defined to include a tangible medium such as a memory, DVD, CD, etc. storing the software and/or firmware.

FIGS. 3, 4, 5, 7, 8, and 10 are flow diagrams representative of machine readable and executable instructions or processes that can be executed to implement the example systems, apparatus, and article of manufacture described herein. The example processes of FIGS. 3, 4, 5, 7, 8, and 10 can be performed using a processor, a controller and/or any other suitable processing device. For example, the example processes of FIGS. 3, 4, 5, 7, 8, and 10 can be implemented in coded instructions stored on a tangible medium such as a flash memory, a read-only memory (ROM) and/or random-access memory (RAM) associated with a processor (e.g., the processor 1312 of FIG. 13). Alternatively, some or all of the example processes of FIGS. 3, 4, 5, 7, 8, and 10 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 3, 4, 5, 7, 8, and 10 can be implemented manually or as any combination(s) of any of the foregoing techniques, for example, any combination of firmware, software, discrete logic and/or hardware. Further, although the example processes of FIGS. 3, 4, 5, 7, 8, and 10 are described with reference to the flow diagrams of FIGS. 3, 4, 5, 7, 8, and 10, other methods of implementing the processes of FIGS. 3, 4, 5, 7, 8, and 10 can be employed. For example, the order of execution of the blocks may be changed, and/or some of the blocks described may be changed, eliminated, sub-divided, or combined. Additionally, any or all of the example processes of FIGS. 3, 4, 5, 7, 8, and 10 can be performed sequentially and/or in parallel by, for example, separate processing threads, processors, devices, discrete logic, circuits, etc.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A medical device interface system comprising:
   a device interface to connect a medical device to a client system and to enable exchange of data between the medical device and the client system, the device interface comprising:
     a plug and play detector to detect a connection of the medical device to the device interface; and
     a serial agent, including:
       a processor, to gather information from the medical device via a connection between the medical device and the device interface and to select an appropriate device driver to operate and interact with the medical device connected to the device interface regardless of a presence or absence of an existing plug and play capability of the medical device, the serial agent to operate with the plug and play detector to execute a plug and play program sequence with the medical device when the medical device is a plug and play medical device, and to transform the medical device into a plug and play medical device via a non-plug and play program sequence when the medical device is a non-plug and play medical device using a common device driver configured to be used for both plug and play and non plug and play medical devices, the client system including a message and data exchange service to communicate with the medical device via the device interface;
     a core, said core comprising:
       a common service layer;
       a network server to communicate with the client system over a data communication interface;
       an interface eXtensible Markup Language (iXML) engine to parse inbound iXML messages and to build outbound iXML messages; and
       a driver engine to manage a plurality of medical device drivers and to form a pool of threads for device driver execution;
     one or more device driver threads; and
     one or more adapters.

2. The interface system of claim 1, further comprising the medical device having a unique identifier facilitating identification and communication with the client system via the device interface.

3. The interface system of claim 1, wherein the iXML engine comprises a session manager and an XML generator and wherein the driver engine comprises:
   a driver manager to transmit a device update to a USB detector;
   a driver storage; and
   a connection detector.

4. The interface system of claim 3, wherein the connector detector comprises a universal serial bus (USB) detector to generate a class holding at least one USB information object in response to receiving the device update from the driver manager.

5. The interface system of claim 1, where the device interface is to transform a USB connecting device into a plug and play connectivity device communicating with the client system via the serial agent.

6. The interface system of claim 1, wherein the device interface is to convert between a universal serial bus (USB) data communication protocol and an RS-232 data communication protocol.

7. A machine-implemented method for interfacing between a medical device and a clinical information system, said method comprising:
   detecting, using a device interface having a serial agent, a presence of a medical device on a network including a clinical information system, the serial agent including:
     a core, said core comprising:
       a common service layer;
       a network server to communicate with the clinical information system over a data communication interface;
       an interface eXtensible Markup Language (iXML) engine to parse inbound iXML messages and to build outbound iXML messages; and
       a driver engine to manage a plurality of medical device drivers and to form a pool of threads for device driver execution;
     one or more device driver threads; and
     one or more adapters;
   gathering information from the medical device connected to the device interface;
   searching a device driver repository at the device interface for an object and one or more associated device drivers to represent the medical device;
   registering the medical device with the clinical information system using the object; and
   interacting with the medical device using the one or more associated device drivers to communicate between the medical device and the clinical information system, wherein interacting comprises executing a plug and play program sequence with the medical device when the medical device is a plug and play medical device and transforming the medical device into a plug and play medical device via a non-plug and play program sequence when the medical device is a non-plug and play medical device using a common device driver configured to be used for both plug and play and non plug and play medical devices, the clinical information system including a message and data exchange service to communicate with the medical device via the device interface.

8. The method of claim 7, further comprising retrieving a medical device identifier stored at the medical device and creating a unique identifier for the medical device to facilitate communication between the medical device and the clinical information system via the device interface.

9. The method of claim 7, wherein the iXML engine comprises a session manager and an XML generator and wherein the driver engine comprises a driver manager, a driver storage, and a connection detector.

10. The method of claim 9, wherein the connector detector comprises a universal serial bus (USB) detector.

11. The method of claim 7, where the device interface transforms a USB connecting device associated with the medical device into a plug and play connectivity device communicating with the clinical information system via the serial agent.

12. The method of claim 7, wherein the device interface converts between a universal serial bus (USB) data communication protocol and an RS-232 data communication protocol.

13. The method of claim 7, wherein the device interface exchanges messages with the clinical information system via interface eXtensible Markup Language (iXML).

14. An article of manufacture comprising:
a computer readable storage medium; and
executable program instructions embodied in the computer readable storage medium that when executed by a programmable system cause the programmable system to implement a medical device interface system comprising:
a device interface routine connecting a medical device to a client system and enabling exchange of data between the medical device and the client system, the client system including a message and data exchange service to communicate with the medical device via the device interface, the device interface routine comprising:
a plug and play detector detecting a connection of the medical device to the device interface; and
a serial agent gathering information from the medical device via a connection between the medical device and the device interface and selecting an appropriate device driver to operate and interact with the medical device connected to the device interface regardless of a presence or absence of an existing plug and play capability of the medical device, the serial agent operating with the plug and play detector to execute a plug and play program sequence with the medical device when the medical device is a plug and play medical device, and to transform the medical device into a plug and play medical device via a non-plug and play program sequence when the medical device is a non-plug and play medical device using a common device driver configured to be used for both plug and play and non plug and play medical devices, the serial agent including:
a core, said core comprising:
a common service layer;
a network server to communicate with the clinical information system over a data communication interface;
an interface eXtensible Markup Language (iXML) engine to parse inbound iXML messages and to build outbound iXML messages; and
a driver engine to manage a plurality of medical device drivers and to form a pool of threads for device driver execution; one or more device driver threads; and
one or more adapters.

* * * * *